(12) United States Patent
Butrick

(10) Patent No.: US 9,452,230 B2
(45) Date of Patent: Sep. 27, 2016

(54) WASHER/DISINFECTOR

(71) Applicant: AMERICAN STERILIZER COMPANY, Mentor, OH (US)

(72) Inventor: Craig Anthony Butrick, Painesville, OH (US)

(73) Assignee: AMERICAN STERILIZER COMPANY, Mentor, OH (US)

( * ) Notice: Subject to any disclaimer, the term of this patent is extended or adjusted under 35 U.S.C. 154(b) by 419 days.

(21) Appl. No.: 14/260,391

(22) Filed: Apr. 24, 2014

(65) Prior Publication Data

US 2015/0305818 A1    Oct. 29, 2015

(51) Int. Cl.
*A61L 2/18*    (2006.01)

(52) U.S. Cl.
CPC . *A61L 2/18* (2013.01); *A61B 90/70* (2016.02)

(58) Field of Classification Search
CPC ............. A61L 2/07; A61L 2/18; A61L 2/20; A61L 2/22; A61L 2202/17; A61L 2202/24; A61B 90/70
See application file for complete search history.

(56) References Cited

U.S. PATENT DOCUMENTS

| | | | |
|---|---|---|---|
| 3,789,860 A | 2/1974 | Katterheinrich et al. | 134/104 |
| 4,235,642 A | 11/1980 | Federighi et al. | 134/58 |
| 4,576,792 A | 3/1986 | Mårtensson | 422/27 |
| 6,432,216 B1 | 8/2002 | Thies | 134/18 |
| 7,079,759 B2 | 7/2006 | Tokutake et al. | 392/394 |
| 7,108,000 B2 | 9/2006 | Lagace | 134/98.1 |
| 7,841,104 B2 | 11/2010 | Robert et al. | 34/225 |
| 2005/0072449 A1 | 4/2005 | Alpert et al. | 134/25.1 |
| 2007/0253869 A1* | 11/2007 | Robert | A61L 2/18 422/400 |
| 2008/0236625 A1 | 10/2008 | Kim et al. | 134/18 |
| 2009/0183753 A1* | 7/2009 | Maennle | A47L 15/0021 134/18 |
| 2011/0048342 A1 | 3/2011 | Vroom | 122/367.1 |
| 2011/0126861 A1 | 6/2011 | Dorigo et al. | 134/22.1 |
| 2014/0150827 A1* | 6/2014 | Martineau | B08B 3/02 134/26 |

* cited by examiner

*Primary Examiner* — Timothy Cleveland
(74) *Attorney, Agent, or Firm* — Kusner & Jaffe; Michael A. Centanni

(57) ABSTRACT

A washer/disinfector having a washing chamber dimensioned to receive articles to be washed. The washing chamber has a sump at the bottom thereof for collecting fluids used in the washing chamber. A fluid-heating system comprised of a steam generator is connected to a steam-to-fluid heat exchanger. The fluid-heating system has an exhaust port disposed in the washing chamber for exhausting residual steam from the heat exchanger into the washing chamber.

3 Claims, 1 Drawing Sheet

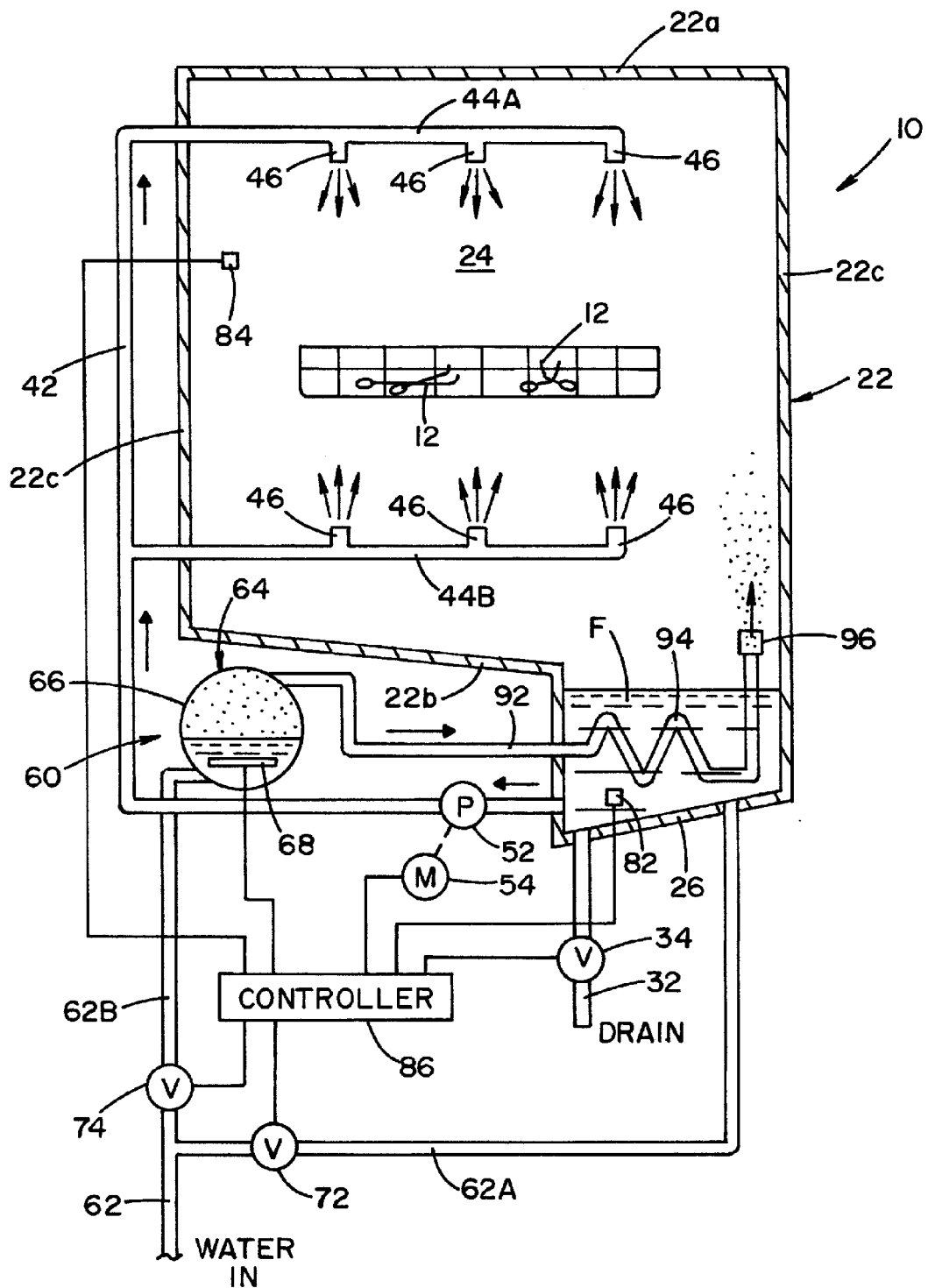

WASHER/DISINFECTOR

FIELD OF THE INVENTION

The present invention relates generally to the cleaning and decontaminating arts, and more particularly to washers and disinfectors for washing and disinfecting instruments and equipment, such as surgical, medical, dental, veterinary and mortuary instruments and equipment that contain or potentially contain, biological contaminants.

BACKGROUND OF THE INVENTION

Medical washers are conventionally known and are used to clean instruments and equipment that are exposed to biological contaminants. Such washers typically clean the instruments and equipment by directing jets or streams of fluid at the instrument and/or equipment from spray heads or nozzles located within the washer. A typical cleaning operation may include a preliminary rinse cycle, a pre-wash cycle, and a wash cycle (where the instruments and equipment are exposed to one or more chemical cleaning solutions), a rinse cycle and a thermal rinse cycle.

During these various phases of a washing cycle, fluids are introduced into the washing chamber by pumps to effect the washing or rinsing of the articles to be cleaned. The fluids used within the washing chamber during the different cycles often have significantly different temperatures. For example, during a pre-wash phase, cold water from a facility's cold water lines (i.e., tap water) is typically used. The wash phase typically uses water from the facility's water lines (with added detergents and chemicals), the water being heated within the washing chamber to about 150° F. (The heating of fluids within the washer typically occurs in a sump located at the bottom of the washing chamber where the washing fluids are collected). The rinse phase typically uses hot water from the facility's hot water line. A thermal rinse typically uses pure, high-quality water that is heated within the washer to about 190° F.

It is known to heat the fluids used in a medical washer using electric-heating systems or steam-heating systems. The use of electric-heating systems generally produces longer cycle times and lower performance because electricity cannot economically be used at the levels necessary to provide the desired heating. Steam is more economical, but the use of steam in medical washers presents other problems. In this respect, fewer and fewer medical facilities have steam systems available, let alone steam systems that can provide high-quality steam that is required in medical washers. Moreover, the steam condensate, which results after steam is used in the heat exchanger, is often merely directed to a drain in the building's facilities. In one respect, this represents a loss of energy. In another respect, cold potable water is often used to cool down the steam condensate to a temperature acceptable for discharge to a drain. This further consumes another valuable resource.

The present invention provides a washer/disinfector having a steam-heating system for heating fluids used in the washer/disinfector wherein residual steam and steam condensate are exhausted from the steam-heating system into the washer/disinfector.

SUMMARY OF THE INVENTION

In accordance with a preferred embodiment of the present invention, there is provided a washer/disinfector comprising a washing chamber dimensioned to receive articles to be washed. The washing chamber has a sump at the bottom thereof for collecting fluids used in the washing chamber. Sprayers are provided within the chamber for directing fluid onto the articles to be washed. A fluid circulation system circulates fluids from the sump to the sprayers. A fluid-heating system comprised of a steam generator is connected to a steam-to-fluid heat exchanger. The fluid-heating system has an exhaust port disposed in the washing chamber for exhausting residual steam from the heat exchanger into the washing chamber. Sensors within the chamber monitor the temperature and humidity within the washing chamber. A controller controls the amount of steam to the heat exchanger to control the temperature of the fluid in the washing chamber.

An advantage of the present invention is a washer/disinfector for washing medical instruments.

Another advantage of the present invention is a washer/disinfector as described above having heating means for heating fluids used therein.

A still further advantage of the present invention is a washer/disinfector as described above wherein a steam-to-fluid heat exchanger is provided to heat fluids used in the washer/disinfector.

Another advantage of the present invention is a washer/disinfector as described above wherein a steam-to-fluid heat exchanger is disposed in a sump in a washing chamber of the washer/disinfector to heat fluids in the sump.

Another advantage of the present invention is a washer/disinfector as described above wherein steam condensate and residual steam from the heat exchanger are exhausted into the washing chamber.

These and other advantages will become apparent from the following description of a preferred embodiment taken together with the accompanying drawings and the appended claims.

BRIEF DESCRIPTION OF THE DRAWINGS

The present invention may take physical form in certain parts and arrangement of parts, preferred embodiments of which will be described in detail in the specification and illustrated in the accompanying drawings which form a part hereof, and wherein:

FIG. 1 is a schematic view of a washer illustrating one embodiment of the present invention.

DETAILED DESCRIPTION OF PREFERRED EMBODIMENT

Referring now to the drawings wherein the showings are for the purpose of illustrating preferred embodiments of the invention only, and not for the purpose of limiting same, FIG. 1 schematically illustrates a medical washer 10 for washing medical instruments and equipment 12, such as, by way of example and not limitation, surgical, medical, dental, veterinary and mortuary instruments and equipment.

Washer 10 includes a housing 22 having a top wall 22a, a bottom wall 22b and side walls 22c. Housing 22 defines a washing chamber 24. Housing 22 is formed to include a sloped sump 26 that is disposed at the bottom of washing chamber 24. As will be described in greater detail below, sump 26 is provided to receive washing fluids or rinsing fluids, designated "F" in the drawing, that are used in washing chamber 24. A drain line 32 is formed in the bottom of sump 26. A valve 34 is provided within drain line 32 to control the flow of washing fluids or rinsing fluids F therethrough. A circulation conduit 42 communicates with sump 26 and connects sump 26 to first and second sprayer arms 44A, 44B having spray nozzles 46 therein. First sprayer arm 44A is disposed in the upper portion of washing chamber 24 with spray nozzles 46 directed downward. Second sprayer arm 44B is disposed in the lower portion of washing chamber 24 with spray nozzles 46 directed upward. In this respect, spray nozzles 46 direct washing fluids or rinsing fluids F toward the center of washing chamber 24 and medical instruments 12, as illustrated in FIG. 1. A pump 52 is provided within circulation conduit 42 to pump fluids F from sump 26 to spray nozzles 46. Pump 52 is driven by a motor 54, as schematically illustrated in FIG. 1.

Washer 10 includes a fluid-heating system 60 for heating fluids within washing chamber 24. Fluid-heating system 60 is generally comprised of a steam generator 64. A high-quality water supply line 62 has a first branch line 62A that is connected to sump 26 and a second branch line 62B connected to a steam generator 64. Steam generator 64 may be a gas-heated or electric-heated boiler. In the embodiment shown, a boiler 66 includes an electric-heating element 68. A valve 72 is disposed within branch line 62A to control the flow of water from a high-quality water supply source (not shown) to sump 26. A valve 74 is disposed within branch line 62B to control flow of the water from the high-quality, pure water supply source (not shown) to steam generator 64.

A temperature sensor 82 is disposed within sump 26 and a humidity sensor 84 is disposed within washing chamber 24. Sensors 82, 84 are operable to provide electrical signals indicative of the temperature of fluid F in sump 26 and the humidity in washing chamber 24, respectively, to a controller 86. Controller 86 is programmed to control the operation of washer 10. As schematically illustrated in FIG. 1, controller 86 is operatively connected to sensors 82, 84, to receive signals therefrom, and to motor 54 and to valves 34, 72, and 74, to control the operation thereof. Controller 86 is also connected to heating element 68 in boiler 66 to control the operation thereof.

A steam line 92 extends from boiler 66 into sump 26. Steam line 92 is preferably formed into a coil 94 within sump 26 to act as a heat exchanger as shall be described in greater detail below.

Referring now to the operation of washer 10, a preferred washing cycle includes a pre-wash phase, a wash phase, a rinse phase and a thermal rinse phase. At the beginning of the pre-wash phase, a pre-wash fluid is introduced into washing chamber 24. A pre-wash fluid is typically cold water from an external source, i.e., a cold water line from a facility's water system. The cold water generally is at a temperature below room temperature. Controller 86 operates valve 72 to allow cold water to be introduced into sump 26 in washing chamber 24 through branch line 62A of water inlet 62. (A cleaning chemical may be added to the cold water).

When sufficient water is introduced into washing chamber 24, controller 86 closes valve 72. Controller 86 then starts motor 54 that causes pump 52 to pump the cold water to spray arms 44A, 44B to pre-wash instruments 12. After a predetermined period of time, the pre-wash phase is terminated by deactivating motor 54. Controller 86 then opens valve 34 to allow the pre-wash fluid to drain from washing chamber 24. Once washing chamber 24 is drained, valve 34 is closed by controller 86.

Upon completion of the pre-wash phase, a washing phase is initiated. Controller 86 opens valve 72 to allow water to enter into sump 26 of washing chamber 24. When sump 26 is filled with a sufficient amount of water, controller 86 closes valve 72. Based on signals from temperature sensor 82 in sump 26, controller 86 determines whether the water within sump 26 is at a desired temperature (typically about 150° F.) for the washing phase. (As will be appreciated, detergents or other washing chemicals are typically added to the hot water for the wash phase). If the temperature of the water is below a desired washing temperature, controller 86 energizes heating element 68 to bring the washing fluid within sump 26 to the desired washing temperature.

More specifically, controller 86 energizes heating element 68, which heats the water within boiler 66 to form steam. The steam is conveyed through steam line 92 to coil 94 in sump 26. Coil 94 is preferably formed of a metallic material which allows efficient heat transfer from the steam within coil 94 to fluid F in sump 26. Temperature sensor 82 within sump 26 monitors the temperature of fluid F. Once a desired minimum temperature of fluid F is reached, controller 86 deactivates heating element 68.

According to one aspect of the present invention, excess steam and steam condensate formed as the steam passes through coil 94 is conveyed to diffuser 96 within washing chamber 24 wherein excess steam and steam condensate are released into washing chamber 24. Because the steam and steam condensate are sterile, no contamination is introduced into washing chamber 24 by release of the steam and steam condensate. Moreover, introduction of the steam and steam condensate into washing chamber 24 heats the surfaces of washing chamber 24, thereby utilizing residual energy in the steam. In this respect, release of steam into the washing chamber 24 facilitates heating of the space within the washing chamber 24 as well as heating of walls 22a, 22b, 22c of housing 22. The air space within washing chamber 24 and the inner surface of the walls of housing 22 are thus pre-heated prior to initiation of a washing cycle. The introduction of steam and steam condensate into washing chamber 24 gradually heats the surfaces within washing chamber 24. This reduces the likelihood of thermal shock that normally results when streams of hot fluid are introduced into washing chamber 24 during the start of a washing cycle as the heated fluid F from sump 26 is conveyed to spray arms 44A, 44B at the beginning of a washing phase of the cleaning cycle. Introducing excess steam and steam condensate into washing chamber 24 before the start of a washing cycle allows the surfaces and space within washing chamber 24 to gradually increase in temperature thereby reducing any thermal shock thereto that might occur if hot washing fluid is sprayed into the washing chamber 24 and onto racks and side walls 22c of washing chamber 24.

Once the heated washing fluid is at the desired washing temperature, controller 86 energizes motor 54, which in turn energizes pump 52 to pump the heated washing fluid to spray arms 44A, 44B and onto medical equipment 12 to be cleaned. After a predetermined period of time, the wash phase is terminated by deactivating motor 54. Controller 86 then opens valve 34 to allow the wash fluid to drain from washing chamber 24. Once washing chamber 24 is drained, valve 34 is closed by controller 86.

Following the wash phase, a rinse phase is initiated. Controller 86 operates valve 72 to allow water from the facility's water lines into sump 26 of washing chamber 24. Once sump 26 has been filled with the appropriate amount of water, controller 86 closes valve 72 and energizes motor 54 to cause pump 52 to circulate the rinse fluid through rotary spray arms 44A, 44B to rinse washing fluid from instruments 12. After a predetermined period of time, the rinse phase is terminated by deactivating motor 54. Controller 86 then opens valve 34 to allow the rinse fluid to drain from washing chamber 24. Once washing chamber 24 is drained, valve 34 is closed by controller 86.

Following the rinse phase, a thermal rinse phase is preferably performed. The thermal rinse phase is performed using high-quality, pure water from an external source. The pure water is introduced to washing chamber 24 through a fluid inlet line (now shown). Controller 86 allows a pre-determined amount of pure water to enter washing chamber 24. Typically, the pure water would have a temperature at or below room temperature. When a sufficient amount of pure water has filled sump 26, controller 86 causes heating element 68 to heat the pure water to a desired "thermal rinse temperature." Typically, a thermal rinse is conducted at between 180° F. and 194° F. Once the desired thermal rinse temperature has been attained, controller 86 energizes motor 54 that causes pump 52 to pump the heated rinse fluid to spray arms 44A, 44B to rinse medical instruments 12. Following a pre-determined amount of time wherein the instruments are rinsed by the rinse fluid, controller 86 terminates the washing cycle and the heated rinse fluid is drained from chamber 24 through drain line 32, as described above.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. A washer/disinfector, comprising:
a washing chamber dimensioned to receive articles to be washed, said washing chamber having a sump at the bottom thereof for collecting fluids used in said washing chamber;
sprayers within said chamber for directing fluid onto said articles to be washed;
a fluid circulation system for circulating fluids from said sump to said sprayers;
a fluid-heating system comprised of a steam generator connected to a steam-to-fluid heat exchanger, wherein said steam-to-fluid heat exchanger is disposed in said sump, said fluid-heating system having an exhaust port disposed in said washing chamber for exhausting residual steam from said heat exchanger into said washing chamber;
sensors within said chamber for monitoring the temperature and humidity within said washing chamber; and
a controller for controlling the amount of steam to said heat exchanger to control the temperature of said fluid in said washing chamber.

2. A washer/disinfector as described in claim 1, wherein said steam generator comprises a boiler with an electric-heating element.

3. A washer/disinfector as described in claim 1, wherein said heat exchanger is a tubular coil disposed within said sump.

* * * * *